(12) United States Patent
Kim et al.

(10) Patent No.: US 7,485,656 B2
(45) Date of Patent: Feb. 3, 2009

(54) ANTIFUNGAL REMEDY FORMULATION FOR EXTERNAL APPLICATION

(75) Inventors: Sang-Lin Kim, Seoul (KR); Hyun-Kwang Tan, Seoul (KR); Jun-Sik Kim, Ansan-shi (KR); Ho-Beom Lee, Suwon-shi (KR); Geun-Hong Min, Suwon-shi (KR); Hae-Won Ryou, Suwon-shi (KR)

(73) Assignee: Boryung Pharmaceutical Co., Ltd. (KR)

( * ) Notice: Subject to any disclaimer, the term of this patent is extended or adjusted under 35 U.S.C. 154(b) by 700 days.

(21) Appl. No.: 10/467,244

(22) PCT Filed: Feb. 7, 2002

(86) PCT No.: PCT/KR02/00198

§ 371 (c)(1),
(2), (4) Date: Jan. 16, 2004

(87) PCT Pub. No.: WO02/062336

PCT Pub. Date: Aug. 15, 2002

(65) Prior Publication Data

US 2004/0122071 A1  Jun. 24, 2004

(30) Foreign Application Priority Data

Feb. 7, 2001 (KR) .................... 2001/5993

(51) Int. Cl.
*A61K 31/4196* (2006.01)
*A61K 31/41* (2006.01)
*A61K 9/06* (2006.01)

(52) U.S. Cl. .............. 514/383; 514/558; 424/401; 424/404

(58) Field of Classification Search .............. 514/383, 514/558
See application file for complete search history.

(56) References Cited

U.S. PATENT DOCUMENTS

| 4,404,216 | A |   | 9/1983  | Richardson |         |
|-----------|---|---|---------|------------|---------|
| 4,775,678 | A | * | 10/1988 | Su et al.  | 514/396 |
| 5,725,874 | A | * | 3/1998  | Oda et al. | 424/443 |
| 6,143,794 | A | * | 11/2000 | Chaudhuri et al. | 514/655 |

FOREIGN PATENT DOCUMENTS

| EP | 0 096 569 A2 | 12/1983 |
| EP | 0 515 310 A1 | 11/1992 |

\* cited by examiner

*Primary Examiner*—Sreeni Padmanabhan
*Assistant Examiner*—Sahar Javanmard
(74) *Attorney, Agent, or Firm*—Fish & Richardson P.C.

(57) ABSTRACT

An antibacterial composition for external application, particularly, a remedial formulation for external use containing fluconazole is disclosed. The formulation comprises a base material, 0.1-5.0 percent by weight of fluconazole and 1.0-40.0 percent by weight of any one compound selected from a group consisting of fatty acid, fatty alcohol, higher fatty acid ester and lower alcohol based on weight of the base material. The composition according to the present invention has various advantages of a favorable absorption into a system through the skin of a human body and delivery of active material into horny layer of the skin, a reduced skin stimulation and an excellent stability. Therefore, the composition is efficiently useable in a medical treatment application for dermatomycosis-related infectious diseases including tinea pedis, tinea corporis, tinea cruris, tinea versicolor and/or candidiasis and the like.

5 Claims, 2 Drawing Sheets

ANTIFUNGAL REMEDY FORMULATION FOR EXTERNAL APPLICATION

FIELD OF THE INVENTION

The present invention relates an antibacterial or antifungal (hereinafter referred to as "antifungal") composition for external application containing triazole-based agents such as fluconazole as an active component. The composition of the present invention ensures the transfer of active materials deep into the horny layer of skin of a human body system to enhance the treatment effect, absorption and penetration activities thereof.

Particularly, by leading the delivery of the active component through the skin deep into the horny layer, the composition according to the present invention can provide a maximum remedial value of the active component as an antifungal active agent.

BACKGROUND OF THE RELATED ART

It is known that antifungal formulations for external use, more particularly, pharmaceutical compositions containing tolnaftate resistant to fungi and/or bacteria or imidazole derivatives such as clotrimazole, ketoconazole and the like having activity for candida species are generally available for the remedy of diseases related to the fungi including fungal infections.

Such known compositions have an excellent level of activity relative to a variety of microorganisms but, when substantially administrated through the skin of a patient, exhibit poor absorption and/or penetration into the horny layer of the skin, thereby resulting in unsatisfactory treatment. Moreover, when the conventional composition is applied to the skin, it is generally sticky causing an unpleasant feeling or discomfort. Therefore, it is required to improve the feeling or discomfort when appling the composition onto the skin.

Fluconazole, an antifungal active component, which has been developed for oral administration, is not practically used as a remedial formulation for external application.

Hereinbefore, an "oral" formulation means an agent which treats fungal disease by distributing the formulation into the internal parts of the entire body. Thus, for example, when a fluconazole based oral formulation is administered to treat a fungal disease excess dose of the formulation is required to obtain the desired curing value. However, long-term administration of triazole-based drugs may be a burden for the liver and cause undesired distribution for the drug through thereof over the entire body.

Accordingly, there is a pressing need to develop a novel remedial formulation for external use containing said fluconazole as a major active component in order to cure only the fungal infection of skin in a short period of time.

SUMMARY OF THE INVENTION

Accordingly, the present invention is directed to an antifungal composition for external application containing fluconazole that substantially obviates the above problem due to limitation and disadvantage of the related art.

An object of the present invention is to provide an antifungal formulation composition for external application containing fluconazole which is able to penetrate deep into a horny layer of the skin of a patient to maximize the curing activity of the fluconazole and to provide high stability and improved capability of spreading.

The composition according to the present invention serving in the form of an external formulation, rather than other conventional compositions developed and used only as oral formulations, allows the use of fluconazole in treating fungal skin infections without the anxiety of overdosing thereof.

Additional advantages, objects, and features of the invention will be set forth in the description which follows and will become apparent to those having ordinary skill in the art upon examination of the following or may be learned from practice of the invention.

The objectives and other advantages of the invention may be realized and attained by the structure specifically described in the written description and claims hereof as well as the appended drawings.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings are included to provide a further understanding of the invention and are incorporated in and constitute a part of this application. In the drawings.

DETAILED DESCRIPTION

Reference will now be made in detail to the preferred embodiments of the present invention, examples of which are illustrated in the accompanying drawings.

To achieve the object and other advantages and in accordance with the purpose of the invention, the composition according to the present invention provides an antifungal remedy formulation composition for external application comprising (a) 0.1-5.0 percent by weight of fluconazole; (b) 1.0-40.0 percent by weight of any one compound selected from a group consisting of fatty acid, fatty alcohol, higher fatty acid ester and lower alcohol; and (c) a base material as the remainder, all of the components being based on weight of the composition.

As stated above, the formulation according to the present invention containing antifungal active materials can allow the drug to have favorable affinity to skin and spreading ability; improve activity of the active component contained in the formulation; and regulate release of the component into the skin, thereby enhancing drug-retention capacity of the on skin and to secure remedy efficacy over the long-term.

As an embodiment of the composition according to the invention, a cream type formulation prepared in the manner described above comprises the active component suitably dissolved in the base material and, when administered through the skin, can improve activity of the component, control the release of the component and increase retention ability thereof on the skin, thereby ensuring the effect within the body for a long period of time. Further, when adding liquid oil materials, the formulation has excellent spreading capability and subcutaneous absorption of drugs, and is physico-chemically stable and less irritating to the skin.

Accordingly, the inventive formulation can reduce skin stimulation, be favorable to the touch when applied to the skin, exhibits excellent treatment effect over long, be physiologically stable and useable as an antifungal formulation particularly for skin.

The formulation according to the present invention generally means agents in the form of cream, gel, external remedy and so forth which is applicable to the surface of the skin.

With regard to the formulation according to the present invention, the active component (a) "fluconazole" is known to have superior antifungal activity. The drug was disclosed to control the biosynthetic reaction of an important sterol, that is, ergosterol found in cell membrane of the fungi. Additionally, the drug has a higher affinity relative to p-450 enzyme in the fungi whereas it has a lower affinity to alternative p-450 enzyme in a human body whereby it shows selective antifungal performance and little adverse effect of the drug. The formulation of the present invention may contain fluconazole in an amount of about 0.1 to 5% by weight, more preferably about 0.5 to 3.0% by weight.

The formulation of the present invention may further include fatty acid, fatty alcohol, higher fatty acid ester or lower alcohol in an amount of about 1 to 40.0% by weight and, among them, the fatty acid and fatty alcohol are preferably one compound and/or a combination of two or more selected from a group consisting of oleic acid, linoleic acid, linolenic acid, arachidonic acid, oleyl alcohol and lauryl alcohol. Such fatty acid and fatty alcohol may be present in an amount of about 2.0 to 20.0% by weight based on total weight of the composition, more preferably about 2.0 to 10.0% by weight.

The higher fatty acid ester includes any one compound and/or combination of two or more selected from a group consisting of etyl iso-octanoate, isopropyl isostearate, hexyldecyl isostearate, butyl stearate, octyldodecyl neodecanoate, isostearyl palmitate, isopropyl palmitate, isopropyl miristate, octyldodecyl miristate, butyl miristate, hexyldecyl miristate, isopropyl linoleate and etyl linoleate. However, it is not limited to this group but may further include typical saturated, unsaturated higher fatty acid ester and/or animal or vegetable oils. Among the fatty acid ester the formulation according to the present invention preferably contains isopropyl miristate.

Such higher fatty acid. ester may be present in an amount of about 2.0 to 30.0% by weight based on total weight of the composition, more preferably about 2.0 to 20.0% by weight. The higher fatty acid ester is preferably in a liquid state at ordinary normal temperature in order to secure sufficient flow of the active component and ensure rapid diffusion thereof through the skin when the external remedy formulation is applied to the skin.

For lower alcohol used in the formulation of the present invention, $C_1$-$C_4$ alcohols are used and, in particular, any one compound and/or combination of two or more selected from a group consisting of methanol, ethanol(including modified alcohols), propanol, butanol, isopropanol and isobutanol may be contained in the formulation. Such lower alcohol may be present in the formulation in an amount of about 5.0 to 40.0% by weight, more preferably about 5.0 to 30.0% by weight.

Furthermore, The formulation composition of the present invention may selectively contain a base material depending on desired type of the formulation.

Another aspect of the present invention provides a cream type formulation preferably containing a cream base material, wherein the base material comprises 1.0 to 20.0% by weight of non-ionic surfactant, 2.0 to 30.0% by weight of oil-based material and 40.0 to 80.0% by weight of water, based on total composition.

Examples of the non-ionic surfactant presented in the cream base material are polyoxyalkylene surfactants such as alkylene sorbic acid ester, polyoxyalkylene alkylethers, polyoxyalkyleneglycol fatty acid esters and polyoxyalkylene hydrogenated caster oil, sorbitan fatty acid esters sorbitan monostearate, polyoxyethylene sorbitan monostearate, glyceryl monostearate, polyoxyethylene cetylether, polyethyleneglycol monostearate and polyoxyethylene hydrogenated caster oil. Such non-ionic surfactant may be presented in the formulation in an amount of about 1.0 to 20.0% by weight based on the total composition, more preferably about 1.0 to 15.0% by weight.

Further, examples of the oil-based materials are hydrocarbons such as squallene, squallane, light liquid paraffin, micro crystalline wax and cerasine; wax such as beeswax, white wax, spermaceti, carnauba wax; fatty acid esters such as diethyl cebasate, diisopropyl adipate, cetyl palmitate and miristyl miristate; fatty alcohols such as stearyl alcohol, 2-octyldodecanol, 2-hexyldecanol and cetanol; triclycerides such as natural fatty acid triglyceride and medium chain fatty acid triglyceride; and fatty acids such as palmitic acid, stearic acid and miristic acid. However, the oil-based materials are not limited to the above and may further include organic base materials capable being used in the production of typical cream type products. Among them, the aliphatic compounds are preferably saturated aliphatic compounds, in particular, any one or a combination of two or more selected from a group consisting of stearyl alcohol, light liquid paraffin, medium chain fatty acid, triglycerides, diethyl cebasate, octyldodecanol and squallene.

In addition, the cream type formulation may contain about 40.0 to 80.0% by weight of water.

In another aspect of the present invention, a gel type composition preferably includes a gel base material, wherein the get base material comprises 0.1 to 20.0% by weight of a gelling agent, 0.5 to 10.0% by weight of dissolution adjuvant, 2.0 to 10.0% by weight of non-ionic surfactant, 5.0 to 50.0% by weight of lower alcohol and 30.0 to 70.0% by weight of water based on total weight of the composition.

Such gelling agent is by any one compound and/or a combination of two or more selected from a group consisting of carboxyvinyl polymer, polyoxyethylene polyoxypropylene polymer, methylcellulose, hydroxypropyl cellulose, hydroxypropyl methylcellulose, ethylcellulose, gellangum and xanthan gum and is present in the composition in an amount of about 0.1 to 20.0% by weight, more preferably about 0.2 to 15.0% by weight.

The dissolution adjuvant may be any one compound and/or a combination of two or more selected from a group consisting of propylene glycol, polyethylene glycol 300-600, glycerine and sorbitol and be added to the composition in an amount of about 0.5 to 10.0% by weight, preferably 3.0 to 10.0% by weight based on total weight of the composition.

The lower alcohol contained in the gel base material may be by any one compound and/or a combination of two or more selected from a group consisting of methanol, ethanol, propanol, butanol, isopropanol and isobutanol and be presented in the composition in an amount of about 5.0 to 50.0% by weight, preferably 5.0 to 40.0% by weight based on total weight of the composition.

The antifungal formulation according to the present invention may further include various additives, for example, stabilizer, perfume, coloring agent, preservation agent and the like unless its performance is adversely affected by the conventional additives. Particularly, in order to prepare the cream type formulation of the present invention, preferably added is at least one stabilizer. Examples of the additives are antioxidants such as butylhydroxy anisole, dibutylhydroxy toluene or propyl galdate; preserving agents such as paraoxy benzoic ester or dihydro acetic acid; and/or chelating agents such as disodium edetate but are not limited to the same.

The following examples further illustrate the present invention, but the invention is not limited thereto. All amounts and proportions referred to herein and in the appended claims are by weight unless otherwise indicated.

Preparation of cream type antifungal formulation for external application

EXAMPLE 1

Based on 100 g of the produced composition, the components are blended in ratios as described in the following list to form the antifungal formulation for external application according to the present invention.

| | |
|---|---|
| Fluconazole | 1.0 g |
| Cetanol | 6.0 g |
| Stearyl alcohol | 6.0 g |
| Polyethylene glycol 400 | 5.0 g |
| Light liquid paraffin | 5.0 g |
| Sorbitan monostearate | 2.0 g |
| Polysorbate 60 | 3.0 g |
| Polysorbate 80 | 1.0 g |
| Ethanol | 15.0 g |
| Isopropyl miristate | 3.0 g |
| Polyoxyethylene oleylether | 3.0 g |
| Paraoxy benzoic methyl | 0.1 g |
| Paraoxy benzoic propyl | 0.01 g |
| Disodium edetate | 0.02 g |
| Purified water | Proper qt. |
| Total | 100 g |

When the formulation made by blending the said components is produced, oil based components among them are primarily fused at 60 to 70° C. Then, the fused solution is added with the fluconazole dissolved in a portion of the purified water after heating the same while stirring. The resultant solution is mixed with an aqueous phase comprising components other than the above oil based components dissolved in the remaining purified water. Thereafter, by emulsifying the obtained mixture at 70 to 75° C. and cooling the same to room temperature while stirring the final cream type antifungal formulation for external application is obtained.

EXAMPLE 2

In the same manner as illustrated in the example 1, the following relative ratio of respective components are blended to form the desired cream type antifungal formulation for external application.

| | |
|---|---|
| Fluconazole | 1.0 g |
| Stearyl alcohol | 5.0 g |
| Light liquid paraffin | 5.0 g |
| Medium chain fatty acid triglyceride | 12.0 g |
| Glyceryl monostearate | 2.0 g |
| Ethanol | 20.0 g |
| Polyoxyethylene (25) cetylether | 2.0 g |
| Paraoxy benzoic methyl | 0.1 g |
| Paraoxy benzoic butyl | 0.01 g |
| Disodium edetate | 0.02 g |
| Purified water | Proper qt. |
| Total | 100 g |

EXAMPLE 3

Likewise, the relative ratio of respective components below are blended to form the desired antifungal formulation for external application. The resulting product is formed into a cream type formulation in the same manner as described in Example 1.

| | |
|---|---|
| Fluconazole | 1.0 g |
| Cetanol | 5.0 g |
| Light liquid parattin | 6.0 g |
| Diethyl cebasate | 10.0 g |
| Glyceryl monostearate | 4.0 g |
| Polyoxyethylene (25) cetylether | 2.0 g |
| Ethanol | 15.0 g |
| Isopropyl miristate | 1.0 g |
| Paraoxy benzoic methyl | 0.1 g |
| Paraoxy benzoic butyl | 0.01 g |
| Disodium edetate | 0.4 g |
| Purified water | Proper qt. |
| Total | 100 g |

EXAMPLE 4

In this example, the relative ratio of respective components below are combined to form the desired antifungal formulation for external application. The resulting product is formed into a cream type formulation in the same manner as described in Example 1.

| | |
|---|---|
| Fluconazole | 1.0 g |
| Stearyl alcohol | 4.0 g |
| Light liquid paraffin | 5.0 g |
| 2-octyldodecanol | 12.0 g |
| Sorbitan monostearate | 5.0 g |
| Polysorbate 60 | 3.0 g |
| Polyoxyethylene oleylether | 5.0 g |
| Ethanol | 20.0 g |
| Paraoxy benzoic methyl | 0.1 g |
| Paraoxy benzoic butyl | 0.01 g |
| Disodium edetate | 0.2 g |
| Purified water | Proper qt. |
| Total | 100 g |

EXAMPLE 5

Similarly, the relative ratio of respective components below are blended in the same manner as described in Example 1 to form the desired cream type antifungal formulation for external application.

| | |
|---|---|
| Fluconazole | 1.0 g |
| Cetanol | 5.0 g |

| | |
|---|---|
| Light liquid paraffin | 6.0 g |
| White wax | 2.0 g |
| Squallene | 10.0 g |
| Glyceryl monostearate | 3.0 g |
| Ethanol | 15.0 g |
| Polyoxyethylene laurylether | 3.0 g |
| Paraoxy benzoic methyl | 0.1 g |
| Paraoxy benzoic butyl | 0.01 g |
| Disodium edetate | 0.3 g |
| Purified water | Proper qt. |
| Total | 100 g |

EXAMPLE 6

Likewise, the relative ratio of the components below are blended in the same manner as described in Example 1 to form the desired cream type antifungal formulation for external application.

| | |
|---|---|
| Fluconazole | 1.0 g |
| Ethanol | 15.0 g |
| Cetanol | 5.0 g |
| Light liquid paraffin | 6.0 g |
| Medium chain fatty acid triglyceride | 7.0 g |
| Diethyl cebasate | 5.0 g |
| Glyceril monostearate | 3.0 g |
| Polyoxyethylene cetylether | 2.0 g |
| Paraoxy benzoic methyl | 0.1 g |
| Paraoxy benzoic butyl | 0.01 g |
| Disodium edetate | 0.4 g |
| Purified water | Proper qt. |
| Total | 100 g |

EXAMPLE 7

In the same manner as described in Example 1, the respective components below are blended to form the desired cream type antifungal formulation for external application.

| | |
|---|---|
| Fluconazole | 0.5 g |
| Ethanol | 20.0 g |
| Cetanol | 6.0 g |
| Stearyl alcohol | 6.0 g |
| Polyethylene glycol 400 | 5.0 g |
| Light liquid paraffin | 5.0 g |
| Sorbitan monostearate | 2.0 g |
| Polysorbate 60 | 3.0 g |
| Polysorbate 80 | 1.0 g |
| Isopropyl miristate | 3.0 g |
| Polyoxyethylene oleylether | 3.0 g |
| Paraoxy benzoic methyl | 0.1 g |
| Paraoxy benzoic propyl | 0.01 g |
| Disodium edetate | 0.02 g |
| Purified water | Proper qt. |
| Total | 100 g |

COMPARATIVE EXAMPLE 1

Similarly, by using the same method as described in Example 1, the following respective components together are blended to form a cream type antifungal formulation.

| | |
|---|---|
| Fluconazole | 1.0 g |
| Stearyl alcohol | 5.0 g |
| Light liquid paraffin | 6.0 g |
| Glyceryl monostearate | 3.0 g |
| Propylene glycol | 5.0 g |
| Ethanol | 15.0 g |
| Paraoxy benzoic methyl | 0.1 g |
| Paraoxy benzoic butyl | 0.01 g |
| Disodium edepate | 0.4 g |
| Purified water | Proper qt. |
| Total | 100 g |

Preparation of gel type antifungal formulation for external application

EXAMPLE 8

Based on 100 g of the produced composition, its components are blended in a ratio described in the following list to produce a gel type antifungal formulation for external application according to the present invention.

| | |
|---|---|
| Fluconazole | 1.0 g |
| Carboxy vinyl polymer | 0.5 g |
| Polyethylene glycol 400 | 5.0 g |
| Oleic acid | 5.0 g |
| Polyoxylethylene oleylether | 10.0 g |
| Ethanol | 15.0 g |
| Paraoxy benzoic methyl | 0.1 g |
| Paraoxy benzoic butyl | 0.01 g |
| Triethanolamine | 0.45 g |
| Purified water | Proper qt. |
| Total | 100 g |

In order to produce the gel type formulation using the above components, the process is started by swelling the carboxyvinyl polymer in a portion of the purified water and adding water-soluble components among said components to the swollen material. Then, the resultant solution is mixed with other components soluble in ethanol among said components to produce a mixture. Thereafter, the mixture is added to an aqueous phase under stirring. Finally, by adding triethanolamine to the stirred mixture to control the pH level and further adding purified water to form a constant weight, a gel type antifungal formulation is obtained.

EXAMPLE 9

In the same manner as described in Example 8, the respective components below are blended to form the desired gel type antifungal formulation for external application

| | |
|---|---|
| Fluconazole | 2.0 g |
| Carboxyvinyl polymer | 0.5 g |
| Polyethylene laurylether | 10.0 g |
| Cepigel 501 | 6.0 g |
| Polyethylene glycol 400 | 5.0 g |
| Ethanol | 15.0 g |
| Paraoxy benzoic methyl | 0.1 g |
| Paraoxy benzoic butyl | 0.01 g |
| Triethanolamine | 0.4 g |
| Purified water | Proper qt. |
| Total | 100 g |

EXAMPLE 10

| | |
|---|---|
| Fluconazole | 1.0 g |
| Polyoxyethylene polyoxypropylene polymer | 12.0 g |
| Ethanol | 30.0 g |
| Propylene glycol | 5.0 g |
| Polyoxylethylene oleylether | 5.0 g |
| Paraoxy benzoic methyl | 0.1 g |
| Paraoxy benzoic butyl | 0.01 g |
| Purified water | Proper qt. |
| Total | 100 g |

In order to produce a gel type antifungal formulation for external application with the above components in this example, the process is started by adding and dissolving the polyoxyethylene polyoxypropylene polymer in a portion of the purified water under heat of about 80° C. or more. Then, the resultant solution is mixed with the other components after dissolving them in ethanol and is cooled to room temperature, thereby resulting in the gel type antifungal formulation.

EXAMPLE 11

| | |
|---|---|
| Fluconazole | 1.0 g |
| Polyoxyethylene polyoxypropylene polymer | 13.0 g |
| Ethanol | 35.0 g |
| Polyethylene glycol 400 | 5.0 g |
| Polyoxylethylene oleylether | 5.0 g |
| Lauryl alcohol | 5.0 g |
| Paraoxy benzoic methyl | 0.1 g |
| Paraoxy benzoic butyl | 0.01 g |
| Purified water | Proper qt. |
| Total | 100 g |

By using the same manner as described in Example 10, the respective components above are blended to form the desired gel type antifungal formulation for external application.

EXAMPLE 12

| | |
|---|---|
| Fluconazole | 0.5 g |
| Carboxyvinyl polymer | 0.5 g |
| Polyethylene glycol 400 | 5.0 g |
| Linoleic acid | 5.0 g |
| Polyoxylethylene oleylether | 10.0 g |
| Ethanol | 20.0 g |
| Paraoxy benzoic methyl | 0.1 g |
| Paraoxy benzoic butyl | 0.01 g |
| Triethanolamine | 0.45 g |
| Purified water | Proper qt. |
| Total | 100 g |

In the same manner as described in Example 8, the respective components above are blended to form the desired gel type antifungal formulation for external application.

COMPARATIVE EXAMPLE 2

| | |
|---|---|
| Fluconazole | 1.0 g |
| Carboxyvinyl polymer | 0.5 g |
| Polyethylene glycol 400 | 15.0 g |
| Ethanol | 15.0 g |
| Paraoxy benzoic methyl | 0.1 g |
| Paraoxy benzoic butyl | 0.01 g |
| Triethanolamine | 0.4 g |
| Purified water | Proper qt. |
| Total | 100 g |

In the same manner as described in Example 8, the respective components above are blended to form the desired gel type antifungal formulation for external application.

COMPARATIVE EXAMPLE 3

| | |
|---|---|
| Fluconazole | 1.0 g |
| Polyoxyethylene polyoxypropylene polymer | 13.0 g |
| Ethanol | 30.0 g |
| propyleneglycol | 5.0 g |
| Polyethylene glycol 400 | 5.0 g |
| Paraoxy benzoic methyl | 0.1 g |
| Paraoxy benzoic butyl | 0.01 g |
| Purified water | Proper qt. |
| Total | 100 g |

In this comparative example, the components above are blended in the same manner as described in Example 10 to form the desired gel type antifungal formulation for external application.

Efficacy Test of antifungal formulation for external application

EXPERIMENTAL EXAMPLE 1

(Efficacy Test)

The formulations according to the present invention prepared as described were subjected to the remedial efficacy test, especially for tinea disease as follows:

First, the test was initiated by selecting several guinea pigs and cutting hair from four parts selected on their back side. Then, the animals were inoculated by a strain solution containing tinea sycosis TiM M1189 strain. Five days after the inoculation, the formulation to be tested was applied to the guinea pigs once per day for 14 days. Lesion scores as a result of the above experiment were classified:

+1 : a few red spots (or erythema) were monitored to spread like as an island form or to be recovered and grow new hair;

+2 : a number of red spots were present on the epidermal surface and widely spread on infected portions;

+3 : locally monitored was serious inflammation such as an enlarged flare and abscess to be generated in substantial volume or size; and +4 : thick scale formed on the infected area monitored.

Figure 1:
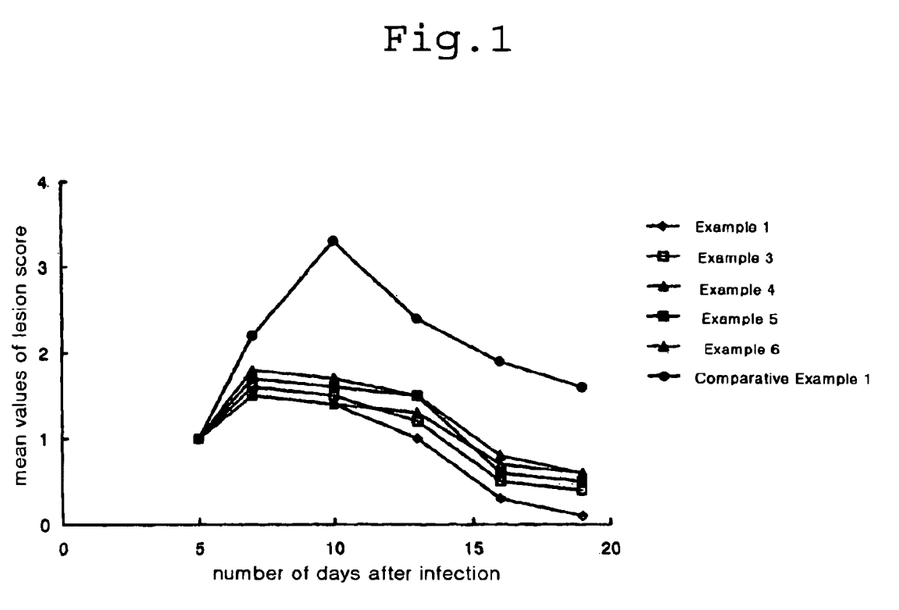
FIG. 1 is a graph showing the result of a test implemented in Example 1 (efficacy test) for a cream type formulation according to the present invention, wherein it illustrates a relative relation between number of days after infection and the mean values of lesion score.
Figure 2:
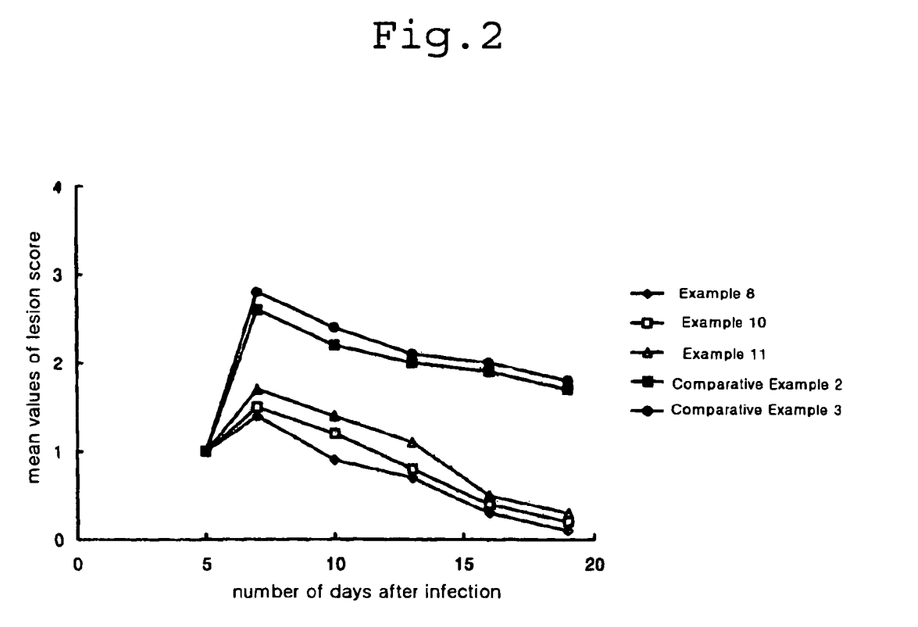
FIG. 2 is another graph showing the result of a test implemented in Example 1 (efficacy test) for a gel type formulation according to the present invention, wherein it illustrates a relative relation between number of days after infection and the mean values of lesion score.

A result of the above experiment is illustrated in FIGS. 1 and 2. As shown in the drawings, it is expected that the antifungal formulation according to the present invention for external application has improved absorption and transfer performances of active materials through the skin into the horny layer of the skin, whereby it is made available as an effective remedy for various fungal infectious diseases such as dermatomycosis-related infectious diseases.

EXPERIMENTAL EXAMPLE 2

(Safety Test)

The antifungal formulation according to the present invention was subjected to a skin stimulation test as follows:

First, 30 pieces of commercially obtainable adhesive plasters for testing red spots were applied with the formulations. The applied pieces was attached to about 30 normal persons. At 1 hour and 24 hour after removing the plaster piece, the area applied with the present formulation was monitored for the degree of red spots (that is, degree of skin stimulation). Consequently, the conditions of the red spots were indicated as "±" or "+" depending on whethr the spots were moderated or noticeably increased, the degree of the red spot generation being the percent of the red spot generating area relative to total area. A result of the above experiment is shown in the following Tables 1 and 2.

TABLE 1

|  | Measuring after 1 hour | | Measuring after 24 hour | |
| --- | --- | --- | --- | --- |
|  | ± | ± | ± | ± |
| Example 1 | 0 | 0 | 0 | 0 |
| Example 3 | 0 | 0 | 0 | 0 |
| Example 4 | 0 | 0 | 0 | 0 |
| Exmaple 5 | 0 | 0 | 0 | 0 |
| Example 6 | 1.5 | 0 | 0 | 0 |
| Comparative Example 1 | 10.8 | 4.8 | 3.1 | 1.9 |

TABLE 2

|  | Measuring after 1 hour | | Measuring after 24 hour | |
| --- | --- | --- | --- | --- |
|  | ± | ± | ± | ± |
| Example 8 | 0 | 0 | 0 | 0 |
| Example 10 | 5.3 | 0 | 0 | 0 |
| Example 11 | 4.8 | 0 | 0 | 0 |
| Comparative Example 2 | 1.2 | 0 | 0 | 0 |
| Comparative Example 3 | 10.2 | 4.8 | 3.1 | 1.9 |

As shown in the above Tables, it was found that the antifungal formulation according to the present invention has few red spots, in turn, no stimulation to the skin.

EXPERIMENTAL EXAMPLE 3

(Stability Test)

The antifungal formulation according to the present invention was subjected to a stability test as follows:

First, the respective formulations were stored in a temperature calibrated bath at 40° C. for six months. Thereafter, chemical and/or physical properties and residual content of the formulations were determined. A results of the above experiment are listed in the following Table 3.

TABLE 3

|  | Chemical/physical properties | Residual rate (%) |
| --- | --- | --- |
| Example 1 | − | 99.8 |
| Example 2 | − | 99.7 |
| Example 3 | − | 99.2 |
| Example 4 | − | 99.5 |
| Example 5 | − | 99.4 |
| Example 6 | − | 99.6 |
| Example 7 | − | 100.0 |
| Example 8 | − | 99.5 |
| Example 9 | − | 99.2 |
| Example 10 | − | 99.5 |
| Example 11 | − | 99.5 |
| Example 12 | − | 99.6 |
| Comparative Example 1 | + | 97.6 |
| Comparative Example 2 | − | 98.3 |
| Comparative Example 3 | − | 99.5 | properties:
no change (−)
little yellowed, separated (+)

As shown in the above Table 3, it was found out that the cream type and gel typ antifungal formulations according to the present invention did not exhibit a change of the chemical and/or physical properties, nor separation states, and had substantially constant residual content. Accordingly, it will be understood that the inventive formulation can ensure stability over time.

As described above, the present invention provides an antifungal formulation composition for external application containing fluconazole, wherein the composition allows the active component, that is, the fluconazole to be speedily absorbed into the horny layer of the skin of a patient so that it can effectively treat fungi and related diseases; in the case where the formulation is spread onto the skin, has no stimulations such as flaring thereby minimizing side effects; is only minimally changeable in chemical and/or physical properties thereof; and has no substantial reduction in residual content even when stored for a long time, increasing its stability.

Particularly, compared with conventional formulations which have been developed and used in oral administration form, the present inventive formulation is useable as an external remedy to eliminate the overdose of fluconazole introduced into the human body. Consequently, the present invention can enhance the practical application performance of the antifungal formulation containing fluconazole.

The above description of the present invention is intended to be illustrative, and not to limit the scope of the claims. Many alternatives, modifications, and variations will be apparent to those skilled in the art.

What is claimed is:

1. Antifungal remedy formulation composition for external application consisting of (a) 0.1-5.0 percent by weight of fluconazole; (b) 2.0-30.0 percent by weight of higher fatty acid ester; (c) 1.0-40.0 percent by weight of at least one compound selected from a group consisting of fatty acid, lower alcohol, lauryl alcohol, oleyl alcohol, stearyl alcohol, 2-octyldodecanol, 2-hexyldecanol and cetanol; and (d) a cream base material as the balance, all of the components being based on their weight of the composition;

wherein the cream base material comprises 1.0 to 20.0% by weight of non-ionic surfactant, 2.0 to 30.0% by weight of oil-based material and 40.0 to 80.0% by weight of water, based on total composition;

wherein the oil-based material is selected from hydrocarbons, wax, fatty acid esters, stearyl alcohol, 2-octyldodecanol, 2-hexyldecanol, cetanol, triglycerides, and fatty acids.

2. Antifungal remedy formulation composition for external application consisting of (a) 0.1-5.0 percent by weight of fluconazole: (b) 2.0-30.0 percent by weight of higher fatty acid ester: (c) 1.0-40.0 percent by weight of at least one compound selected from a group consisting of fatty acid, lower alcohol, lauryl alcohol, oleyl alcohol, stearyl alcohol, 2-octyldodecanol, 2-hexyldecanol and cetanol: and (d) a gel base material as the balance, all of the components being based on their weight of the composition:

wherein the gel base material comprises 0.1 to 20.0% by weight of a gelling agent, 0.5 to 10.0% by weight of dissolution adjuvant, 2.0 to 10.0% by weight of non-ionic surfactant, 5.0 to 50.0% by weight of lower alcohol and 30.0 to 70.0% by weight of water, based on total weight of the composition.

3. A method for preparing a cream type antifungal remedy formulation which comprises mixing the components of composition as claimed in claim 1.

4. A method for preparing a gel type antifungal remedy formulation which comprises mixing the components of composition as claimed in claim 2.

5. Antifungal remedy formulation composition for external application consisting of (a) 0.1-5.0 percent by weight of fluconazole; (b) 2.0-30.0 percent by weight of higher fatty acid ester; (c) 1.0-40.0 percent by weight of a $C_1$-$C_4$ alcohol; and (d) a cream base material as the balance, all of the components being based on their weight of the composition;

wherein the cream base material comprises 1.0 to 20.0% by weight of non-ionic surfactant, 2.0 to 30.0% by weight of oil-based material and 40.0 to 80.0% by weight of water, based on total composition;

wherein the oil-based material is selected from hydrocarbons, wax, fatty acid esters, stearyl alcohol, 2-octyldodecanol, 2-hexyldecanol, cetanol, triclycerides, and fatty acids.

* * * * *

UNITED STATES PATENT AND TRADEMARK OFFICE
CERTIFICATE OF CORRECTION

PATENT NO. : 7,485,656 B2
APPLICATION NO. : 10/467244
DATED : February 3, 2009
INVENTOR(S) : Sang-Lin Kim Page 1 of 1

It is certified that error appears in the above-identified patent and that said Letters Patent is hereby corrected as shown below:

In Column 1, line 5, insert

--Cross Reference
This application claims priority of International Application No. PCT/KR02/00198 filed Feb. 7, 2002, which claims priority of Foreign Patent Application No. 2001/05993 filed Feb. 7, 2001.--

Signed and Sealed this

Twenty-seventh Day of April, 2010

David J. Kappos
*Director of the United States Patent and Trademark Office*